United States Patent
Oliver (10) Patent No.: US 8,740,855 B2
(45) Date of Patent: Jun. 3, 2014

(54) SAFETY NEEDLE SYRINGE BRAKING SYSTEM

(75) Inventor: Richard B. Oliver, Anaheim, CA (US)

(73) Assignee: Credence Medsystems, Inc., Menlo Park, CA (US)

( * ) Notice: Subject to any disclaimer, the term of this patent is extended or adjusted under 35 U.S.C. 154(b) by 118 days.

(21) Appl. No.: 13/176,162

(22) Filed: Jul. 5, 2011

(65) Prior Publication Data

US 2011/0264052 A1 Oct. 27, 2011

Related U.S. Application Data

(63) Continuation of application No. 11/728,783, filed on Mar. 27, 2007, now Pat. No. 7,972,301.

(60) Provisional application No. 60/788,796, filed on Apr. 3, 2006.

(51) Int. Cl.
*A61M 5/315* (2006.01)
*A61M 5/00* (2006.01)

(52) U.S. Cl.
USPC .............................. 604/220; 604/110; 604/225

(58) Field of Classification Search
USPC .................. 604/110, 220, 221, 223, 225, 229
See application file for complete search history.

(56) References Cited

U.S. PATENT DOCUMENTS

| | | | |
|---|---|---|---|
| 4,744,791 A * | 5/1988 | Egolf | 604/229 |
| 4,766,908 A | 8/1988 | Clement | |
| 4,838,869 A | 6/1989 | Allard et al. | |
| 4,950,241 A | 8/1990 | Ranford | |
| 4,966,593 A | 10/1990 | Lennox | |
| 5,019,043 A | 5/1991 | Pastor et al. | |
| 5,085,640 A | 2/1992 | Gibbs | |
| 5,195,985 A | 3/1993 | Hall | |
| 5,211,630 A | 5/1993 | Schmahmann | |
| 5,215,015 A | 6/1993 | Iida et al. | |
| 5,215,533 A | 6/1993 | Robb | |
| 5,226,893 A | 7/1993 | Kayser | |
| 5,334,155 A | 8/1994 | Sobel | |
| 5,336,185 A | 8/1994 | Lynch et al. | |
| 5,344,403 A | 9/1994 | Lee | |
| 5,385,551 A | 1/1995 | Shaw | |
| 5,389,076 A | 2/1995 | Shaw | |
| 5,423,758 A | 6/1995 | Shaw | |
| 5,458,576 A | 10/1995 | Haber et al. | |
| 5,578,011 A | 11/1996 | Shaw | |
| 5,578,015 A | 11/1996 | Robb | |
| 5,601,534 A | 2/1997 | Turner | |
| 5,632,733 A | 5/1997 | Shaw | |
| 5,658,257 A | 8/1997 | Ryles | |
| 5,681,292 A | 10/1997 | Tober et al. | |
| 5,868,713 A | 2/1999 | Klippenstein | |

(Continued)

*Primary Examiner* — Nathan R Price
(74) *Attorney, Agent, or Firm* — K&L Gates LLP; Andrew L. Reibman (57) ABSTRACT

A braking mechanism for a retractable safety syringe is disclosed herein. In a first embodiment, the braking mechanism is disposed about the distal end of a piston. The braking mechanism may comprise a friction material about a post attached to a piston. The friction material is displaced from a seat to a landing when the piston is traversed to a fully extended position to disengage the braking mechanism. In a second embodiment, the braking mechanism is disposed at a proximal end of a syringe body. The braking mechanism has a friction member which engages an outer surface of a rigid shaft of a plunger. The friction member is selectively pivotable to disengage the braking mechanism.

22 Claims, 7 Drawing Sheets

(56) References Cited

U.S. PATENT DOCUMENTS

| | | |
|---|---|---|
| 5,964,735 A | 10/1999 | Alexander |
| 5,971,964 A | 10/1999 | Donaldson |
| 6,010,486 A | 1/2000 | Carter et al. |
| 6,015,438 A | 1/2000 | Shaw |
| 6,033,385 A | 3/2000 | Liu |
| 6,036,674 A | 3/2000 | Caizza et al. |
| 6,050,977 A | 4/2000 | Adams |
| 6,090,077 A | 7/2000 | Shaw |
| 6,193,695 B1 * | 2/2001 | Rippstein, Jr. ............ 604/195 |
| 6,368,303 B1 | 4/2002 | Caizza |
| 6,413,236 B1 | 7/2002 | Van Dyke |
| 6,632,198 B2 | 10/2003 | Caizza |
| 6,712,787 B1 | 3/2004 | Dysarz |
| 6,840,291 B2 | 1/2005 | Caizza et al. |
| 6,953,449 B2 | 10/2005 | Huang |
| 6,986,756 B2 | 1/2006 | Pelkey et al. |
| 7,104,970 B2 | 9/2006 | Chen |
| 7,118,552 B2 | 10/2006 | Shaw et al. |
| 7,147,621 B2 | 12/2006 | Kiehne |
| 7,220,247 B2 | 5/2007 | Shaw et al. |
| 8,137,324 B2 * | 3/2012 | Bobst ............ 604/220 |
| 2001/0053886 A1 | 12/2001 | Caizza |
| 2002/0193736 A1 | 12/2002 | Kiehne |
| 2003/0023205 A1 | 1/2003 | Botich et al. |
| 2003/0212362 A1 | 11/2003 | Roser |
| 2004/0024357 A1 | 2/2004 | Pelkey et al. |
| 2004/0116857 A1 | 6/2004 | Kiehne |
| 2005/0038394 A1 | 2/2005 | Schwarzbich |
| 2006/0089593 A1 | 4/2006 | Landau et al. |
| 2006/0089594 A1 | 4/2006 | Landau |
| 2006/0178625 A1 | 8/2006 | Lim et al. |
| 2007/0135764 A1 | 6/2007 | Chen |
| 2012/0022467 A1 * | 1/2012 | Shovary et al. ............ 604/220 |

* cited by examiner

SAFETY NEEDLE SYRINGE BRAKING SYSTEM

CROSS-REFERENCE TO RELATED APPLICATIONS

This application is a continuation of and claimed priority to U.S. application Ser. No. 11/728,783 filed Mar. 27, 2007, which claims the benefit under 35 U.S.C. §119 (e) to U.S. Provisional Application Ser. No. 60/788,796 filed Apr. 3, 2006, the entire contents Of all of which are hereby incorported by reference in their entirety.

STATEMENT RE: FEDERALLY SPONSORED RESEARCH/DEVELOPMENT

Not Applicable

BACKGROUND

The present invention relates to a retractable safety syringe, and more particularly, to a braking mechanism to resist a retraction force during normal operation of the retractable safety syringe until a piston head engages a needle holder and needle to then withdraw the needle holder and needle within the safety syringe body.

Retractable safety syringes are known in the art. For example, one type of retractable safety syringe is disclosed in U.S. Pat. No. 6,413,236 issued to Van Dyke, the entire contents of which are incorporated herein by reference. In the '236 patent, a retractable safety syringe has a piston which engages a needle holder and needle and retracts the same via a retraction force created by a variable vacuum compartment. In the retractable safety syringe disclosed in the '236 patent, the user must continuously apply a thumb pressure on the thumb platform such that the piston is not inadvertently traversed to a retracted position during operation of the safety syringe. For example, the piston may be inadvertently traversed to the retracted position while medication is being filled in a variable fluid chamber, residual air is being ejected from the variable fluid chamber and medication is being injected into the patient. As such, the user or medical professional is required to receive additional training to operate the safety syringe properly and safely. Unfortunately, the additional training may be costly. Also, since the operation of the safety syringe is not intuitive or fool proof, mistakes may be made during operation of the safety syringe.

Accordingly, there is a need in the art for an improved safety syringe.

BRIEF SUMMARY

The retractable safety syringe disclosed herein addresses the needs discussed above, below and those that are known in the art.

In a first embodiment of the retractable safety syringe, a braking mechanism is disposed adjacent a distal end of the safety syringe. In particular, the braking mechanism may comprise a friction material attached to a piston of the safety syringe. The friction material frictionally engages the inner surface of the syringe body to resist traversal of the piston head toward a retracted position. The braking mechanism may also comprise a punch attached to the distal end of the syringe body. When the piston head is traversed between the retracted position and an extended position, the friction material maintains frictional engagement with the inner surface of the syringe body. When the piston head is traversed to the fully extended position, the punch disengages the friction material from the inner surface of the syringe body.

The friction material may be attached to the piston head via two tines. The two tines may define a seat and a landing. When the friction material is disposed about the seat, the friction material frictionally engages the inner surface of the syringe body producing a friction force greater than or equal to about a retraction force of a variable vacuum compartment. When the friction material is disposed about the landing, the friction material creates a friction force against the inner surface of the syringe body which is less than the retraction force created by the variable vacuum compartment.

The punch may have a fulcrum which intersects the interface between the friction material and the two tines when the piston head is traversed to the fully extended position. The punch may also have a frusto-conical surface which engages the distal ends of the two tines and is operative to inwardly displace the two tines to release the friction material from the seat. As the piston head is traversed from the extended position to the fully extended position, the frusto-conical surface displaces the two tines inwardly and the punch pushes the friction material off of the seat and onto the landing. The tines have pawl surfaces which spring outwardly and engage cam edges of the needle holder when the piston head is traversed to the fully extended position. At this point, the retraction force then withdraws the needle and needle holder into the syringe body.

In a second embodiment of the retractable safety syringe, a second embodiment of the braking mechanism is provided. The second embodiment of the braking mechanism may comprise a base member and a friction member which are pivotable with respect to each other about a joint. The friction member has an up position and a down position. In the up position, an inner edge of a central aperture formed in the friction member frictionally engages a rigid shaft. Such frictional engagement produces a friction force which is greater than or equal to about the retraction force of the variable vacuum compartment. As the piston head is traversed between the retracted position and the extended position during operation of the safety syringe, the friction force of the friction member prevents traversal of the piston head toward the retracted position.

When the piston head is traversed to the fully extended position, a bottom surface of a thumb platform pushes down on the top surface of the friction member to traverse the friction member to the down position. In the down position, a pawl of the friction member engages a cam of the base member. As such, the friction member is not permitted to pivot back to the up position. Also, at the down position, the inner edge of the central aperture of the friction member disengages the outer surface of the rigid shaft thereby reducing or eliminating the friction force. The piston head also engages the needle and needle holder via any means that are known in the art or by means discussed in the first embodiment. Since the friction force of the friction member no longer acts on the outer surface of the rigid shaft, the retraction force of the variable vacuum compartment then withdraws the needle holder and needle into the body of the safety syringe.

BRIEF DESCRIPTION OF THE DRAWINGS

These and other features and advantages of the various embodiments disclosed herein will be better understood with respect to the following description and drawings, in which like numbers refer to like parts throughout, and in which:

FIG. 6 is an enlarged assembled view of FIG. 2a;

DETAILED DESCRIPTION

Referring now to the drawings which are for the purpose of illustrating preferred embodiments of a retractable safety syringe 10 and not for the purpose of limiting the same, FIGS. 1-7C illustrate a first embodiment of the retractable safety syringe 10. Also, FIGS. 8-11 illustrate a second embodiment of the retractable safety syringe 10.

Figure 1:
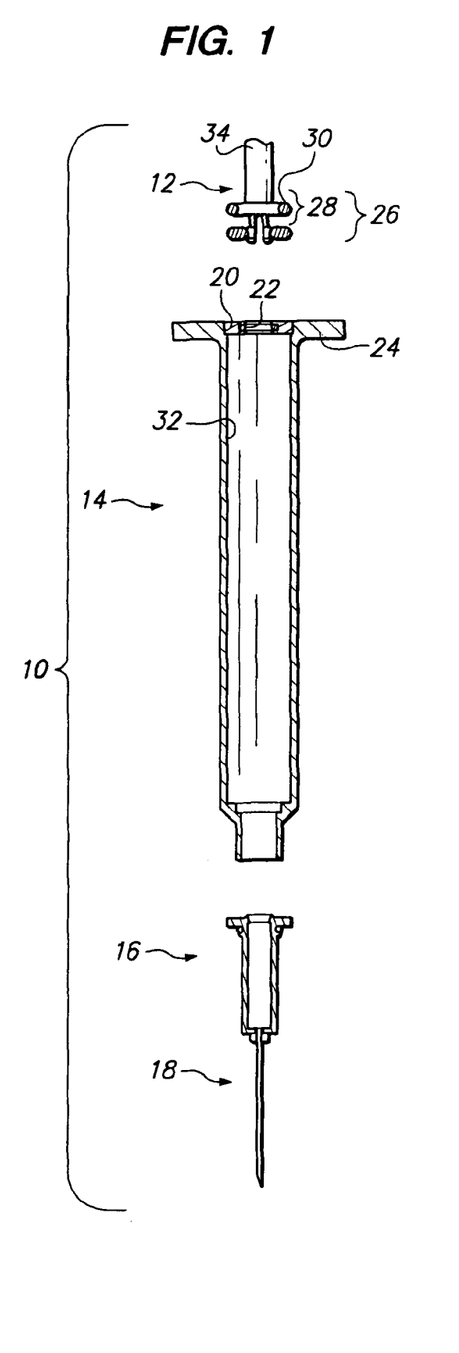
FIG. 1 is an exploded front view of a safety syringe illustrating a first embodiment of a braking mechanism.
Figure 2:
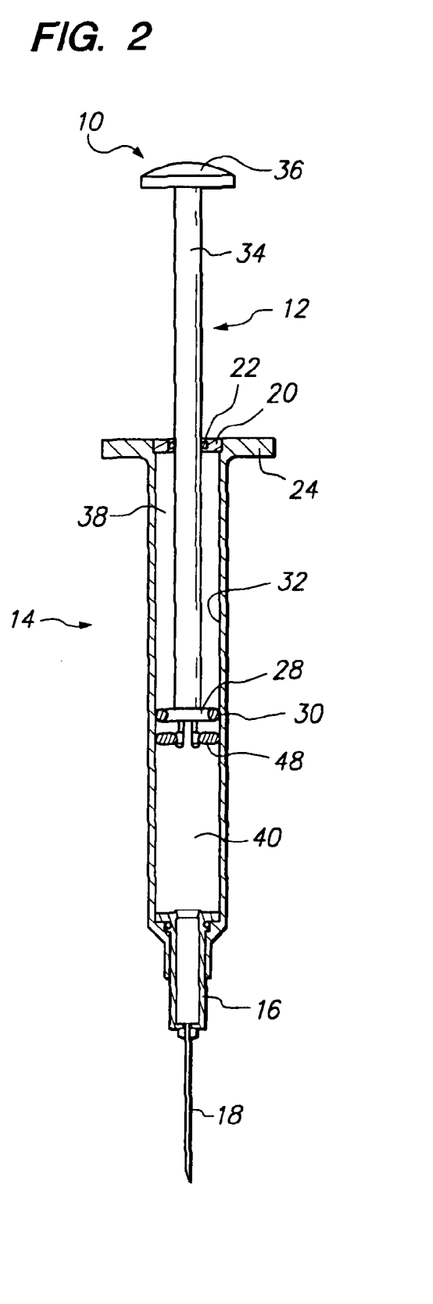
FIG. 2 is an assembled front view of the safety syringe of FIG. 1.

FIG. 1 is an exploded view of the first embodiment of the retractable safety syringe 10. FIG. 2 is an assembled view of the first embodiment of the retractable safety syringe 10 shown in FIG. 1. A plunger 12 is disposed at a proximal side of a syringe body 14. Also, a needle holder 16 and needle 18 are disposed at a distal side of the syringe body 14. An attachment base 20 may be attached to a proximal end of the syringe body 14. Furthermore, a first seal 22 may be disposed about an inner periphery of the attachment base 20. Finger platforms 24 may also be formed at the proximal end of the body 14 which may be utilized to operate the syringe 10.

The plunger 12 may have a piston 26 (see FIG. 1) disposed within the syringe body 14, as shown in FIG. 2. The piston 26 may have a piston head 28 and a second seal 30 which is in sealing contact with the piston head 28 and an inner surface 32 of the syringe body 14. The second seal 30 forms an air tight and a fluid tight seal between the piston head 28 and inner surface 32 of the syringe body 14. The plunger 12 may also have a rigid shaft 34 connected to the piston head 28 and extended through the proximal end of the syringe body 14 (see FIG. 2). The rigid shaft 34 may be in sealing contact with the first seal 22. The first seal 22 also forms an air tight and a fluid tight seal between the attachment base 20 and the rigid shaft 34. A thumb platform 36 may also be attached to the rigid shaft 34 at a proximal end thereof.

The thumb platform 36 and the finger platforms 24 work in conjunction with each other such that the user may depress the thumb platform 36 toward the finger platform 24 by pressing the thumb platform 36 with his/her thumb. This traverses the piston head 28 from a retracted position (see FIGS. 2 and 6) to an extended position or first extended position (see FIG. 3) or a fully extended position or second extended position (see FIG. 5). The piston head 28 may also be traversed from the extended position or first extended position to the retracted position by simultaneously pulling on the thumb platform 36 while pushing on the finger platforms 24. In relation to the first embodiment of the safety syringe, generally, the retracted position is when the piston 26 is closer to the proximal end of the body 14 than the distal end of the body. But, the retracted position may include situations when the piston 26 does not contact the needle holder 16 and the piston 26 is closer to the distal end of the body 14 than the proximal end of the body 14. The extended position or first extended position is generally when the piston 26 is closely adjacent to the needle holder 16 or in contact with the needle holder 16 and the piston 26 is not engaged to the needle holder 16. The fully extended position or second extended position is when the piston 26 is in contact with the needle holder 16 and engaged to the needle holder 16.

The cavity between the first and second seals 22, 30 within the syringe body 14 defines a variable vacuum compartment 38. The variable vacuum compartment 38 creates a retraction force when the piston head is traversed to the extended position or first extended position urging the piston head 28 toward the retracted position. As the piston head 28 is traversed from the retracted position to the extended position (first extended position) or fully extended position (second extended position), the retraction force created by the variable vacuum compartment 38 increases.

The needle holder 16 and needle 18 are disposed or attached to the distal end of the syringe body 14. Furthermore, the cavity between the piston head 28 and the needle holder 16 within the syringe body 14 defines a variable fluid chamber 40 in which fluidic medication may be filled and subsequently injected into a patient.

In operation, the retractable safety syringe 10 is provided to a user or medical professional with the piston head 28 in the retracted position. To fill the variable fluid chamber 40 with medication, the piston head 28 is traversed to the extended position or first extended position by depressing the thumb platform 36 toward the finger platform 24. At the extended position or first extended position, the needle 18 is inserted into a medication container containing fluidic medication. The user then traverses the piston head 28 from the extended position or first extended position to the retracted position thereby filling the variable fluid chamber 40 with medication. The user then inverts the syringe 10 and slightly depresses the thumb platform 36 toward the finger platform 24 to remove any residual air within the variable fluid chamber 40. The user then inserts the needle 18 into the patient's skin and depresses the thumb platform 36 toward the finger platform 24 thereby injecting the medication into the patient.

Figure 2A:
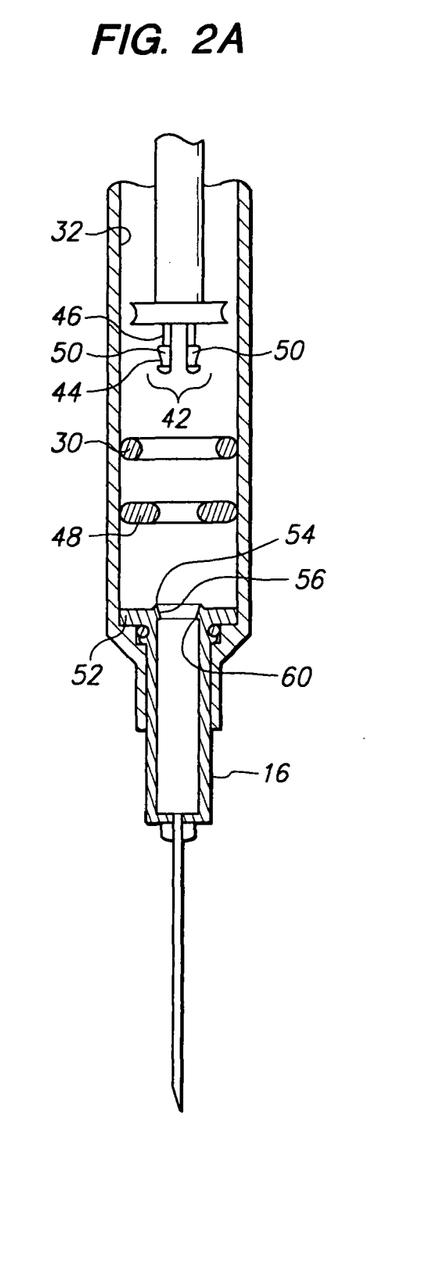
FIG. 2a is an enlarged front view of the safety syringe of FIG. 2 with a second seal unassembled from a piston and a friction material unassembled from two tines.

In the above description of the retractable safety syringe 10, as the piston head 28 is traversed to the extended position or first extended position, the retraction force continuously urges the piston head 28 toward the proximal end of the syringe body 14. But for a braking mechanism, the user must overcome the retraction force by applying continuous pressure on the thumb platform 36 greater than or equal to the retraction force. Fortunately, in the first embodiment of the retractable safety syringe 10, a braking mechanism is incorporated therein to prevent the automatic and unintended retraction of the piston head 28 toward the proximal end of the syringe body 14. In particular, as shown in FIG. 2A, the braking mechanism may have a post 42 defining a seat 44 and a landing 46. A friction material 48 may be disposed about the seat 44 or the landing 46 (see FIGS. 1-3 and 5). When the friction material 48 is disposed about the seat 44, the outer periphery of the friction material 48 engages the inner surface 32 of the syringe body 14 and applies a frictional force thereto which is greater than or about equal to the retraction force of the variable vacuum compartment 38.

Figure 5:
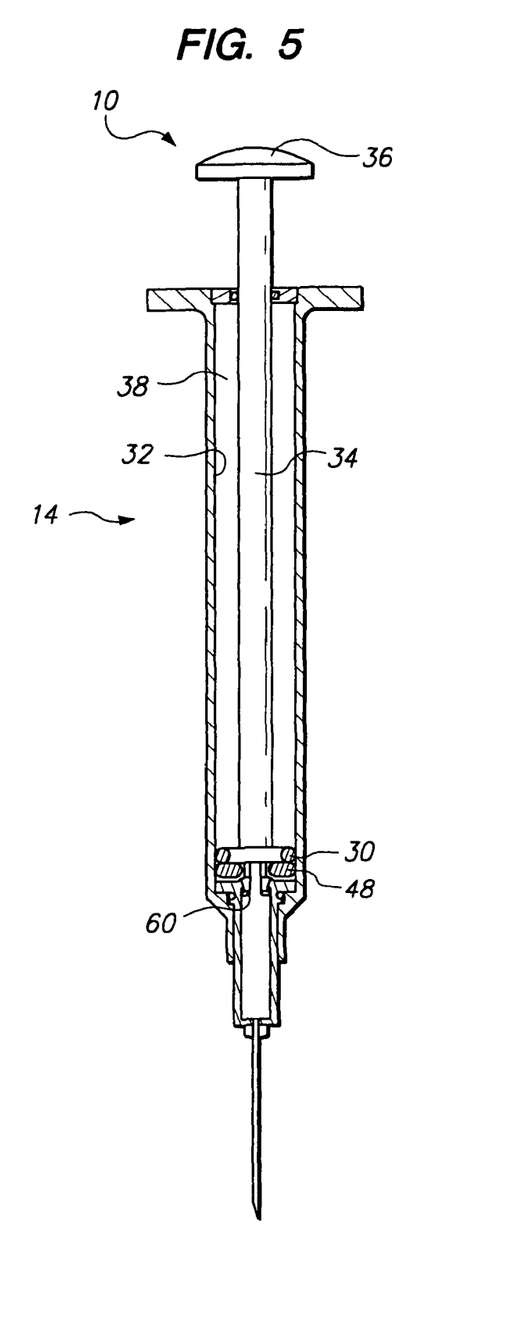
FIG. 5 is a front view of the safety syringe with the friction material disposed about the landing and the piston in a fully extended position.

The friction material 48 is also displaceable from the seat 44 to the landing 46 (see FIG. 5). When the friction material 48 is disposed about the landing 46, the outer periphery of the friction material 48 may create a friction force which is less than the retraction force of the variable vacuum compartment 38. In the above described operation of the retractable safety syringe 10, the friction material is retained about the seat 44 during the entire operation of the retractable safety syringe 10 except when the piston head 28 is traversed to the fully extended position or second extended position (see FIG. 5) at which point, the friction material 48 is displaced from about the seat 44 to about the landing 46.

When the friction material 48 is disposed about the seat 44, the friction material 48 permits the user to traverse the piston 26 between the retracted position and the extended position or first extended position without balancing a pressure applied to the thumb platform 36 and the retraction force of the variable vacuum compartment 38. For example, the user does not have to balance such pressures when the medication is being filled within the variable fluid chamber 40 or air is being removed from the variable fluid chamber 40. The piston head 28 is not permitted to traverse back toward the retracted position via the retraction force thereby the variable fluid chamber 40 is not filled with excessive medication and air is not reintroduced into the variable fluid chamber 40.

To displace the friction material 48 from the seat 44 to about the landing 46, the post 42 may be fabricated from two tines 50 having an upper portion (i.e., landing 46) and a lower portion (i.e., seat 44), as shown in FIG. 2A. The upper portion defines the landing 46 and the lower portion defines the seat 44. The two tines 50 are bendable toward each other by applying a compressive force at the distal ends of the two tines 50. When the compressive force is released, the two tines 50 are displaced outwardly. The upper portion or landing 46 may have an outer periphery which may be sized to an inner periphery of the friction material 48 such that the frictional force of the friction material 48 on the inner surface 32 of the syringe body 14 is less than the retraction force created by the variable vacuum compartment 38 when the friction material 48 is disposed about the landing 46. The outer periphery of the lower portion or seat 44 may be sized to the inner periphery of the friction material 48 such that the frictional force created by the friction material 48 on the inner surface of the syringe body 32 is greater than or about equal to the retraction force of the variable vacuum compartment 38 when the friction material 48 is disposed about the seat 44. To displace the friction material 48 from the seat 44 toward the landing 46, a punch 52 (see FIGS. 2A and 6) may be formed about a proximal end of the needle holder 16 which is operative to push the friction material 48 off of the seat 44 and onto the landing 46. Also, as discussed further below, the punch 52 is operative to inwardly displace the two tines 50 to reduce the outer periphery of the seat 44 thereby permitting the friction material 48 to be displaced from the seat 44 to the landing 46.

Figure 7A:
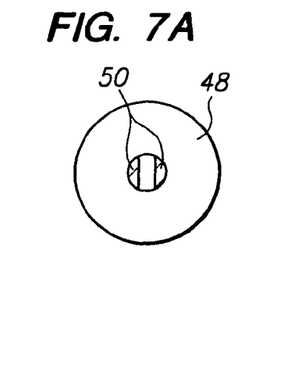
FIG. 7A is a top view of the two tines and a first embodiment of the friction material.
Figure 7B:
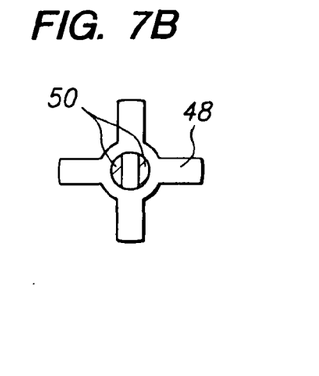
FIG. 7B is a top view of the two tines and a second embodiment of the friction material.
Figure 7C:
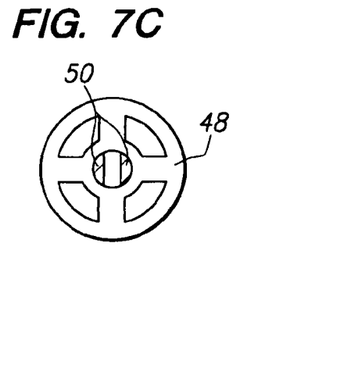
FIG. 7C is a top view of the two tines and third embodiment of the friction material.

The seat 44 of the two tines 50 may have an undercut groove which is sized and configured to receive the friction material 48. The friction material 48 may have various configurations as shown in FIGS. 7A-7C. In FIG. 7A, the friction material 48 has a flat disk configuration; in FIG. 7B, the friction material 48 has a flat cross configuration; and in FIG. 7C, the friction material 48 has flat wheel rim configuration. When the friction material 48 is disposed about the seat 44, the two tines 50 apply an outward force upon the inner periphery of the friction material 48. The under cut groove in combination with the outward force prevents the friction material 48 from being displaced off of the seat 44 as the piston head 28 is traversed between the retracted position and the extended position or first extended position.

Figure 3:
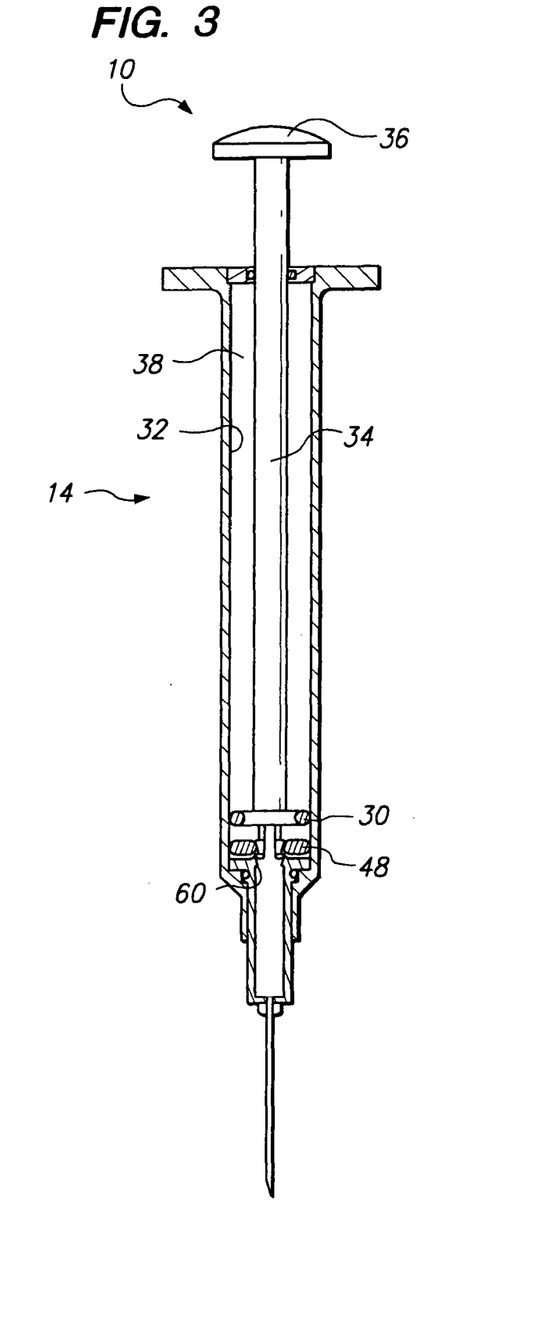
FIG. 3 is a front view of the safety syringe with the friction material engaged to a punch and the piston in an extended position.
Figure 4:
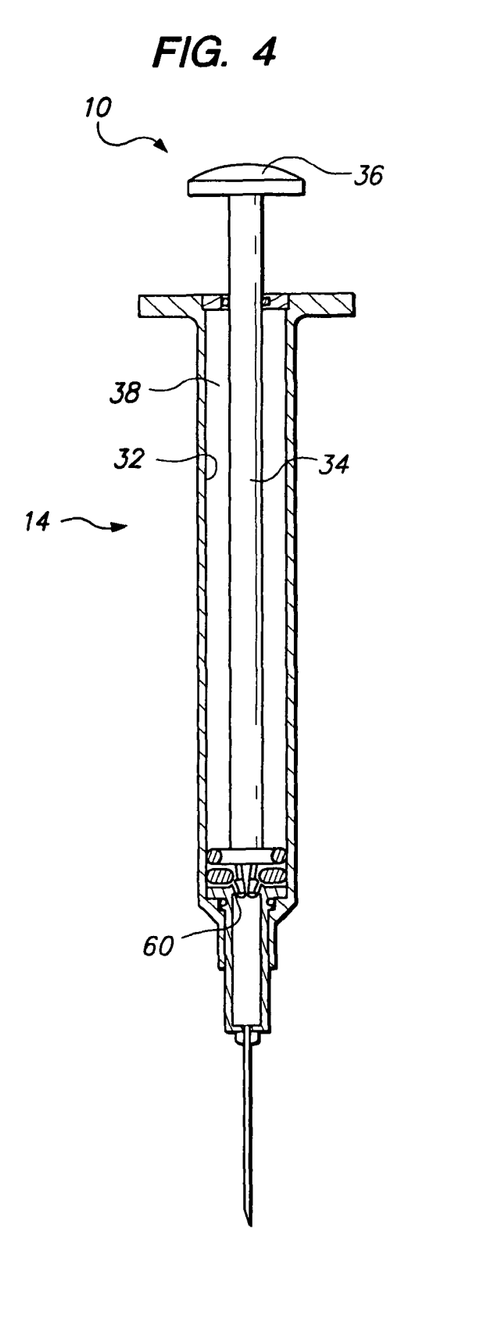
FIG. 4 is a front view of the safety syringe with a fulcrum of a punch intersecting an interface of the friction material and two tines and the friction material being displaced from a seat to a landing.
Figure 6:
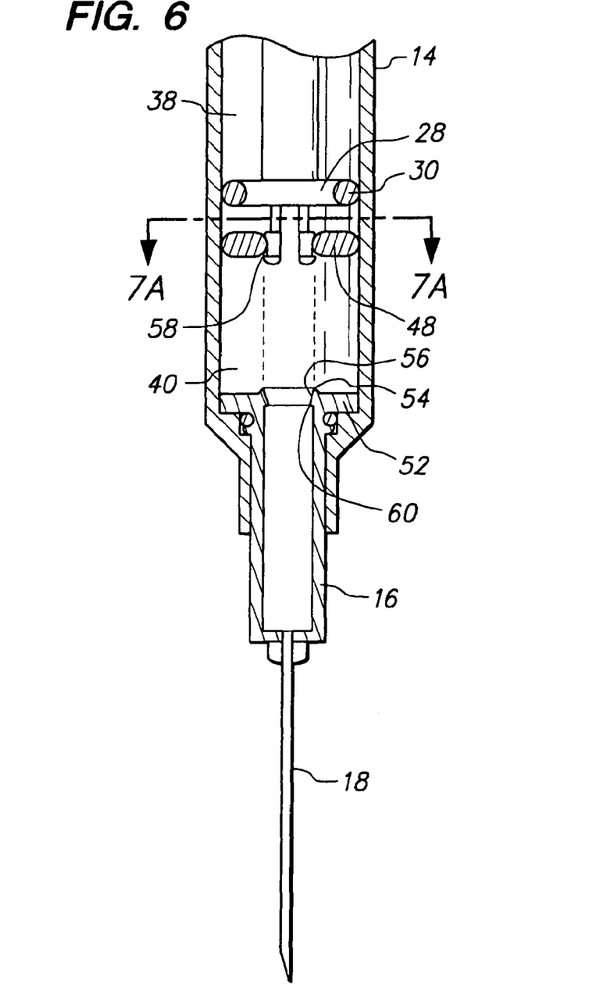

The punch 52 may have a fulcrum 54 and a frusto-conical surface 56, as shown in FIGS. 2A and 6. When the piston 26 is traversed to the extended position or first extended position (see FIG. 3), the fulcrum 54 engages the interface 58 (see FIG. 6) between the friction material 48 and the under cut groove formed in the seat 44. The frusto-conical surface 56 also engages the distal ends of the two tines 50, as shown in FIG. 3. When the piston 26 is further traversed to the fully extended position or second extended position (see FIG. 5), the frusto-conical surface 56 further inwardly displaces the two tines 50 (see FIG. 4) and the punch 52 simultaneously pushes the friction material 48 off of the seat 44 and onto the landing 46. When the friction material 48 is fully displaced off of the seat 44, the under cut groove of the seat 44 may engage a cam edge 60 (see FIGS. 2A, 5 and 6) of the needle holder 16 to positively lock the piston 26 to the needle holder 16 (see FIG. 5). Since the sum of the friction forces between the needle holder 16 and distal end of the body 14 as well as the friction material 48 and the inner surface 32 of body 14 is less than the retraction force, the retraction force of the variable vacuum compartment 38 retracts the needle holder 16 into the syringe body 14.

In operation, the retractable safety syringe 10 of the first embodiment permits the piston 26 to be traversed between the extended position (first extended position) (see FIG. 3) and the retracted position. At any of these positions, due to the braking mechanism, the pressure applied to the thumb platform 36 may be removed without the retraction force of the variable vacuum compartment 38 retracting the piston 26 toward the retracted position. Advantageously, the braking mechanism permits the user to release thumb pressure from the thumb platform 36 during operation of the retractable safety syringe 10 without the piston head 28 being immediately and unintentionally displaced toward the proximal end of the syringe body 14.

When the medication within the variable fluid chamber 40 is being injected into a patient, the piston head 28 is traversed to the fully extended position or second extended position (see FIG. 5). As the piston head 28 is traversed from the extended position or first extended position (see FIG. 3) to the fully extended position or second extended position (see FIG. 5), the punch 52 pushes the friction material 48 off of the seat 44 and onto the landing 46. Also, the frusto-conical surface 56 of the punch 52 inwardly displaces the tines 50 such that the friction material 48 is released from the under cut groove of the seat 44. When the piston 26 is traversed to the fully extended position or second extended position, the friction material 48 is displaced over the landing 46 and the under cut groove of the seat 44 receives the frusto-conical surface 56.

Also, the under cut groove of the seat 44 engages the cam edge 60 of the punch 52. At this point, the sum of the frictional forces exerted on the inner surface of the syringe body 32 by the frictional material 48 as well as the needle holder 16 and the distal end of the body 14 is less than the retraction force created by the variable vacuum compartment 38. The needle holder 16 and needle 18 have a sliding friction fit with the syringe body 14. The retraction force may now withdraw the needle 18 and needle holder 16 within the syringe body 14.

Figure 8:
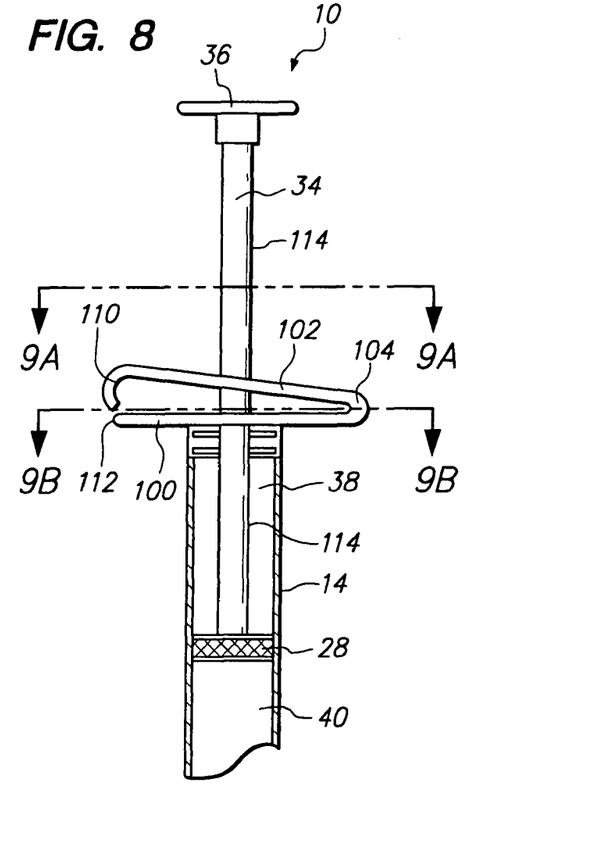
FIG. 8 is a front view of a second embodiment of the braking mechanism disposed about a proximal end of the syringe body.

Referring now to FIGS. 8-11, a second embodiment of the retractable safety syringe 10 is shown for the purposes of illustration and not limitation. In FIG. 8, a second embodiment of the braking mechanism is disposed or attached to a proximal end of the syringe body 14. The braking mechanism has a base member 100 and a friction member 102 which are pivotable with respect to each other about a joint 104. The base member 100 may be wider than the outer diameter of the syringe body 14 and may replace the finger platforms 24 discussed in the first embodiment of the retractable safety syringe 10. The base member 100 may have a central aperture 106 (see FIG. 9B) through which the rigid shaft 34 of the plunger 12 is disposed. As shown in FIG. 9B, the rigid shaft 34 is freely slidable through the central aperture 106 of the base member 100.

Figure 9A:
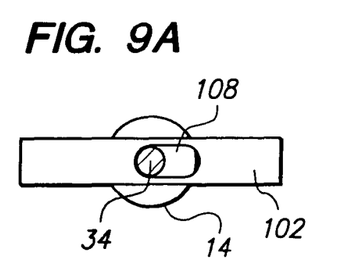
FIG. 9A is a top view of the braking mechanism illustrating an edge of an aperture formed in a friction member in friction engagement with a rigid shaft of the safety syringe.
Figure 9B:
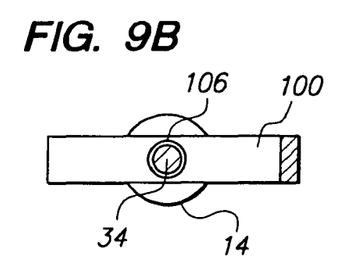
FIG. 9B is a top view of a base member of the braking mechanism with an aperture sized and configured to slidably receive the rigid shaft.
Figure 10:
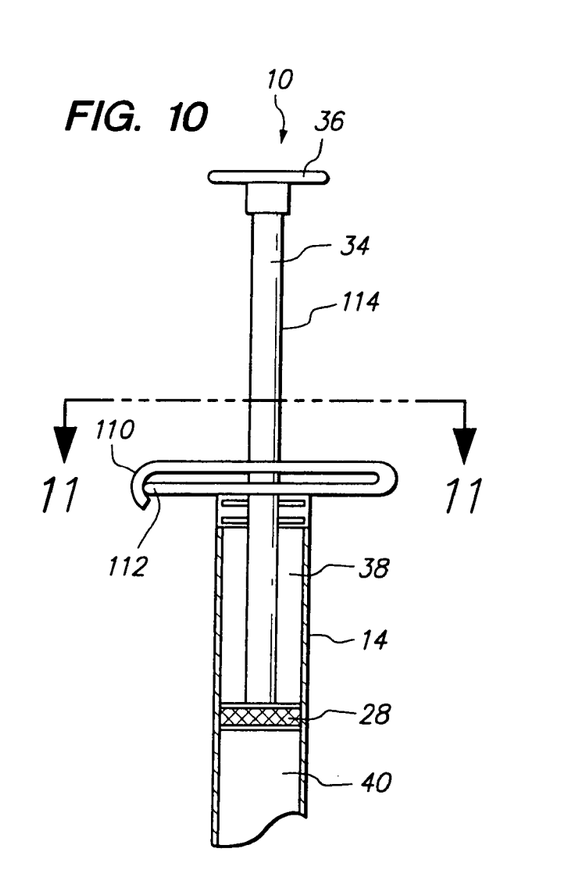
FIG. 10 is a front view of the braking mechanism with the friction member disengaged from the rigid shaft.
Figure 11:
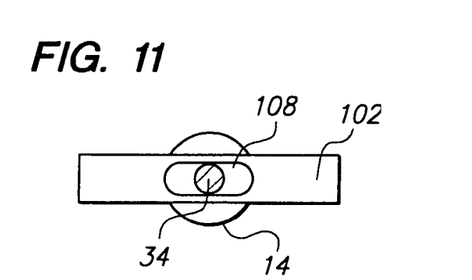
FIG. 11 is a top view of the braking mechanism illustrating that the edge of the aperture formed in the friction member is disengaged from the rigid shaft when the friction member is locked on the base.

The friction member 102 may also have an aperture 108 having an elliptical shape which is sized and configured to engage the rigid shaft 34 when the friction member 102 is in an up position (see FIGS. 8 and 9A) and disengage the rigid shaft 34 when the friction member 102 is in a down position (see FIGS. 10 and 11). In the up position, a pawl 110 of the friction member 102 rides or interferes with a cam 112 formed on a distal end of the base member 100. Also, in the up position, an inner edge of the central aperture 108 formed in the friction member 102 frictionally engages the outer surface 114 of the rigid shaft 34, as shown in FIG. 9A. Such friction engagement may be greater than or equal to about the retraction force created by the variable vacuum compartment 38. Moreover, the frictional forces between the inner edge of central aperture 108 formed in the friction member 102 and the outer surface 114 of the rigid shaft 34 is less than the force required to displace the pawl 110 over the cam 112.

During the step of filling the variable fluid chamber 40 with medication and removing air from the variable fluid chamber 40, the frictional force created between the friction member 102 and the rigid shaft 34 is sufficient to hold the piston head 28 at any position between the retracted position and the extended position or first extended position. When the piston head 28 is traversed to the fully extended position or second extended position, a bottom surface of the thumb platform 36 pushes against the top surface of the friction member 102 until the pawl 110 is permitted to slide over the cam 112 and engage the cam 112 (see FIG. 10). The pawl 110 having a U-shaped or J-shaped configuration locks the cam 112 within a throat of the pawl 110, as shown in FIG. 10. At the down position, as shown in FIG. 11, the inner edge of the central aperture 108 formed in the friction member 102 disengages the outer surface 114 of the rigid shaft 34 thereby eliminating the friction force. When the piston head 28 is traversed to the fully extended position or second extended position, the piston head 28 may be engaged to the needle 18 and needle holder 16 via any method known in the art or via the structure discussed in relation to the first embodiment. At the fully extended position or second extended position, the braking mechanism is disengaged and the retraction force of the variable vacuum chamber 38 withdraws the piston 26, needle 18 and needle holder 16 within the syringe body 14.

In relation to the second embodiment of the safety syringe, generally, the retracted position is when the piston 26 is closer to the proximal end of the body 14 compared to the distal end of the body 14. But, the retracted position may include situations when the piston 26 does not contact the needle holder 16 and the piston 26 is closer to the distal end of the body 14 compared to the proximal end of the body 14. Additionally, at the retracted position, the thumb platform 36 does not contact the friction member 102. The extended position or first extended position is when the piston 26 is closely adjacent to the needle holder 16 or in contact with the needle holder 16 and the piston 26 is not engaged to the needle holder 16. Additionally, at the extended position or first extended position, the thumb platform 36 may be closely adjacent to the friction member 102 or in contact with the friction member 102. Nonetheless, the pawl 110 is not engaged to the cam 112. The fully extended position or second extended position is when the piston 26 is in contact with the needle holder 16 and engaged to the needle holder 16. Also, at the fully extended position the thumb platform 36 may be in contact with the friction member 102.

Figure 12:
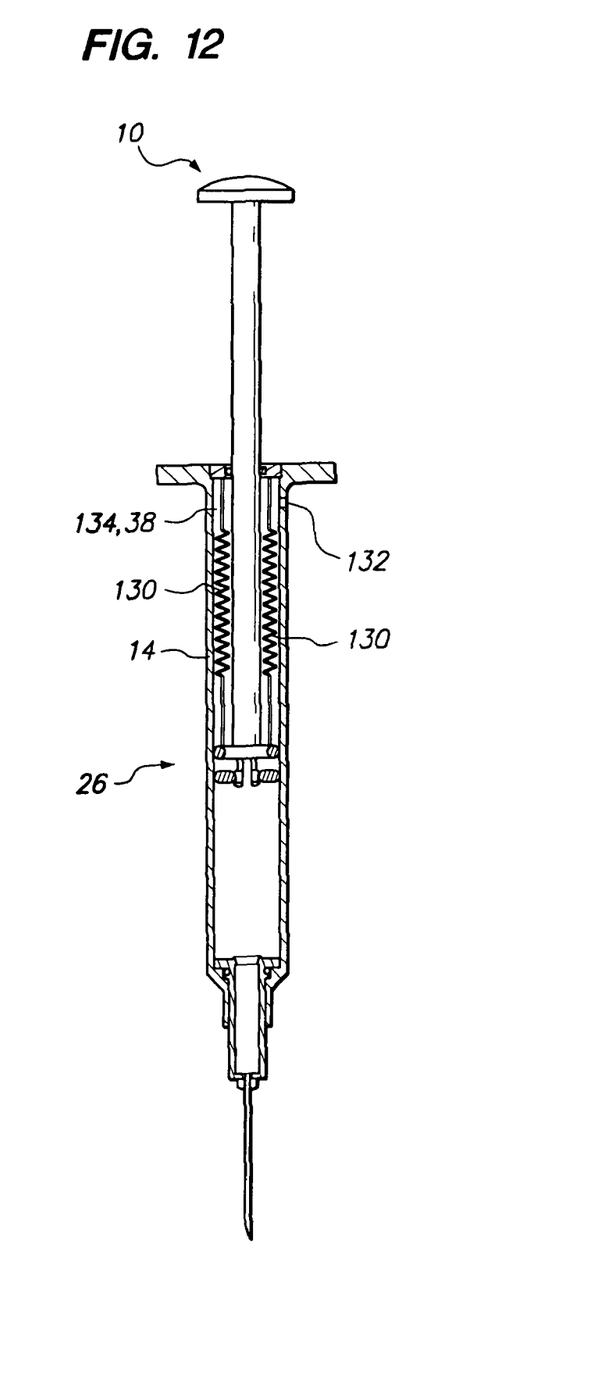
FIG. 12 is an assembled front view of the safety syringe of FIG. 1 wherein a retraction force urging a piston toward a retracted position is created by a tension spring.

In an aspect of the retractable safety syringes 10 of the first and second . embodiments, the braking mechanisms may be employed in retractable safety syringes that are spring activated. For example, FIG. 12 illustrates a retractable safety syringe 10 having a similar configuration to the first embodiment of the safety syringe 10. In particular, the variable vacuum compartment 38 may have at least one but preferably two or more tension springs 130 attached to the proximal end of the body 14 and the piston 26. The tension springs 130 may be relaxed when the piston 26 is in the retracted position. When the piston 26 is traversed toward the extended position (first extended position) or the fully extended position (second extended position), the tension springs 130 are tensioned so as to urge the piston 26 back toward the retracted position. The tension springs 130 may create the retraction force which urges the piston 26 back toward the retracted position. The retraction force created by the tension springs 130 may be in addition to the retraction force created by the variable vacuum compartment 38.

Alternatively, the retraction force created by the tension springs 130 may replace the retraction force of the variable vacuum compartment 38. To this end, an optional air vent 132 may be formed through the body 14 of the syringe 10. The air vent 132 permits air to be introduced into or removed from the cavity 134 previously identified as the variable vacuum compartment 38. When the piston 26 is traversed toward the extended position (first extended position) or the fully extended position (second extended position), air is introduced into the cavity 134 via the air vent 132. Hence, a vacuum is not formed in the cavity 134. Also, when the piston 26 is traversed toward the retracted position, air is removed from the cavity 134 via the air vent 132. Hence, air is not compressed within the cavity 134. When the air vent 132 is formed through the body 14 of the syringe 10, the retraction force is created solely by the tension springs 130. The safety syringe 10 shown in FIG. 13 may be operated in a similar fashion as the first embodiment of the safety syringe 10. Although the tension springs 130 were discussed in relation to the first embodiment of the safety syringe 10, the tension springs 130 may also be employed in the second embodiment of the safety syringe 10.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A retractable safety syringe comprising:
a syringe body having a distal end and a proximal end;
a plunger having a piston disposed within the syringe body, a rigid shaft extending longitudinally through the proximal end of the syringe body, and a thumb platform attached to the rigid shaft configured to traverse the piston distally from a retracted position to a fully extended position, the piston further including a piston seal configured to form a seal between the piston and an inner surface of the syringe body,
an automatic retraction mechanism configured to urge the plunger proximally toward the retracted position;
a braking mechanism adjacent the proximal end of the syringe body, the braking mechanism including a friction member having an eccentrically-shaped through hole that is elongated in a direction substantially transverse to the rigid shaft, the rigid shaft slideably disposed longitudinally through the through hole, the friction member having a first position and a second position, the through hole being in a first through hole position when the friction member is in the first position and a second through hole position when the friction member is in the second position, the first and second through hole positions being offset from each other along a longitudinal axis of the syringe body, an inner edge of the through hole frictionally engages the rigid shaft to resist a retraction force of the retraction mechanism when the friction member is in the first position and the inner edge of the through hole frictionally disengages the rigid shaft when the friction member is in the second position to permit the retraction force to urge the plunger proximally to the retracted position, while still allowing the plunger to be depressed and retracted manually when the friction member is in the first position.

2. The syringe of claim 1, wherein the friction member is rotateable between the first position and the second position.

3. The syringe of claim 1, wherein the friction member further includes a pawl configured to retain the friction member in the second position when the pawl engages the proximal end of the syringe body and the inner edge of the through hole frictionally disengages the rigid shaft.

4. The syringe of claim 3, further comprising a base member, the friction member being pivotably attached to the base member and the pawl being selectively attachable to the base member.

5. The syringe of claim 4, wherein the pawl has a J shape.

6. The syringe of claim 1, wherein a maximum frictional force between the friction member and the rigid shaft when the friction member is in the first position is greater than or equal to about the retraction force of the retraction mechanism.

7. The syringe of claim 1, wherein the retraction mechanism further includes a variable vacuum compartment.

8. The syringe of claim 1, wherein the retraction mechanism further includes a spring.

9. The syringe of claim 1, further comprising:
a needle removably attached to the distal end of the syringe, wherein the plunger is configured to draw the needle into the syringe body when the plunger is retracted by the automatic retraction mechanism.

10. A retractable safety syringe comprising:
a syringe body having a distal end and a proximal end;
a plunger having a piston disposed within the syringe body, a rigid shaft extending longitudinally through the proximal end of the syringe body, and a thumb platform attached to the rigid shaft configured to traverse the piston distally from a retracted position to a fully extended position, the piston further including a piston seal configured to form a seal between the piston and an inner surface of the syringe body,
an automatic retraction mechanism configured to urge the plunger proximally toward the retracted position;
a braking mechanism external to the syringe body, the braking mechanism including a friction member having a through hole, the rigid shaft slideably disposed through the through hole, the friction member having a first position and a second position, the through hole being in a first through hole position when the friction member is in the first position and a second through hole position when the friction member is in the second position, the first and second through hole positions being offset from each other along a longitudinal axis of the syringe body, an inner edge of the through hole frictionally engages the rigid shaft to resist a retraction force of the retraction mechanism when the friction member is in the first position and the inner edge of the through hole frictionally disengages the rigid shaft when the friction member is in the second position to permit the retraction force to urge the plunger proximally to the retracted position, while still allowing the plunger to be depressed and retracted manually when the friction member is in the first position.

11. The retractable safety syringe of claim 10, wherein the braking mechanism also serves as a finger platform for the syringe.

12. The retractable safety syringe of claim 10, wherein the retraction mechanism further includes a variable vacuum compartment.

13. The retractable safety syringe of claim 10 wherein the friction member is rotateable between the first position and the second position.

14. The retractable safety syringe of claim 10, wherein the friction member further includes a pawl configured to retain the friction member in the second position when the pawl engages the proximal end of the syringe body and the inner edge of the through hole frictionally disengages the rigid shaft.

15. The retractable safety syringe of claim 14, further comprising a base member, the friction member being pivotably attached to the base member and the pawl being selectively attachable to the base member.

16. The retractable safety syringe of claim 10, wherein the thumb platform is configured to come into contact with the friction member when the piston is traversed to the fully extended position.

17. The retractable safety syringe of claim 15, wherein the thumb platform is configured to come into contact with the friction member when the piston is traversed to the fully extended position, thereby causing the pawl to attach to the base member.

18. A retractable safety syringe comprising:
a syringe body having a distal end and a proximal end;
a plunger having a piston disposed within the syringe body, a rigid shaft extending longitudinally through the proximal end of the syringe body, and a thumb platform attached to the rigid shaft configured to traverse the piston distally from a retracted position to a fully extended position, the piston further including a piston seal configured to form a seal between the piston and an inner surface of the syringe body, an automatic retraction mechanism configured to urge the plunger proximally toward the retracted position;

a braking mechanism adjacent the proximal end of the syringe body, the braking mechanism including a friction member having a through hole, the rigid shaft slideably disposed through the through hole, the friction member having a first position and a second position, the through hole being in a first through hole position when the friction member is in the first position and a second through hole position when the friction member is in the second position, the first and second through hole positions being offset from each other along a longitudinal axis of the syringe body, an inner edge of the through hole frictionally engages the rigid shaft to resist a retraction force of the retraction mechanism when the friction member is in the first position and the inner edge of the through hole frictionally disengages the rigid shaft when the friction member is in the second position to permit the retraction force to urge the plunger proximally to the retracted position, while still allowing the plunger to be depressed and retracted manually when the friction member is in the first position, the braking mechanism further including a base member positioned perpendicular to rigid shaft, the friction member being pivotably attached to the base member.

19. The syringe of claim 18, wherein the retraction mechanism further includes a variable vacuum compartment.

20. The syringe of claim 18, wherein the friction member is rotateable between the first position and the second position.

21. The syringe of claim 18, wherein the friction member further includes a pawl configured to retain the friction member in the second position when the pawl engages the proximal end of the syringe body and the inner edge of the through hole frictionally disengages the rigid shaft.

22. The syringe of claim 21, wherein the pawl is selectively attachable to the base member.

* * * * *